United States Patent [19]

Müller et al.

[11] Patent Number: 5,095,024

[45] Date of Patent: Mar. 10, 1992

[54] SUBSTITUTED 1,3,4-THIADIZAOLINONES, PROCESSES FOR THEIR PREPARATION, AND THEIR USE FOR COMBATING ENDOPARASITES

[75] Inventors: Nikolaus Müller, Monheim; Gerhard Bonse; Werner Lindner, both of Cologne; Achim Harder, Leverkusen, all of Fed. Rep. of Germany

[73] Assignee: Bayer Aktiengesellschaft, Leverkusen, Fed. Rep. of Germany

[21] Appl. No.: 581,934

[22] Filed: Sep. 13, 1990

[30] Foreign Application Priority Data

Oct. 4, 1989 [DE] Fed. Rep. of Germany ....... 3933092

[51] Int. Cl.$^5$ .................. C07D 285/13; A01N 43/82
[52] U.S. Cl. ..................................... 514/363; 548/142
[58] Field of Search ...................... 548/142; 514/363

[56] References Cited

U.S. PATENT DOCUMENTS

| | | | |
|---|---|---|---|
| 2,799,651 | 7/1957 | Richardson | 548/142 |
| 2,914,547 | 11/1959 | Gaetner | |
| 3,395,234 | 7/1968 | Hopkins et al. | 514/363 |

FOREIGN PATENT DOCUMENTS

| | | |
|---|---|---|
| 0300906 | 1/1989 | European Pat. Off. |
| 2533605 | 2/1977 | Fed. Rep. of Germany |
| 2253515 | 7/1975 | France |
| 2299028 | 8/1976 | France |
| 2299328 | 8/1976 | France |
| 0166360 | 2/1965 | U.S.S.R. |

OTHER PUBLICATIONS

Justus Liebigs Annalen der Chemie, vol. 735, Sep. 9, 1970, pp. 158-188, Weinheim, DE; K. Sasse: "Struktur der Reaktions-produkte aus Thiosemicarbaziden und reaktiven Kohlensäure-Derivaten", p. 172.
Acta Chemica Scandinavica, vol. 23, No. 6, 1969, pp. 1916-1934, Copenhagen, DK; K. A. Jensen et al.: "Studies of Thioacids and Their Derivatives".
Chemical Abstracts, vol. 96, No. 19, May 10, 1982, p. 746, paragraph No. 162591c, Columbus, Ohio, U.S.; I. M. Bazavova et al.: "Study of Dithiocarbamic Acid Derivatives. IX. Arthiocarbohydrazinoylated Compounds with an Active Hydrogen Atom", & Zh. Org. Khim., 1982, 18(1), 213-17.
Chemical Abstracts, vol. 67, No. 7, Aug. 14, 1967, p. 3047, paragraph No. 32383a, Columbus, Ohio, U.S.; Y. Usui et al: "Studies on Fungicides. XIII. Synthesis and Substituted Phenylhydrazine Derivatives and Related Compounds", & Yakugaku Zasshi 87(1), 43-65 (1967).

Primary Examiner—Robert Gerstl
Attorney, Agent, or Firm—Sprung Horn Kramer & Woods

[57] ABSTRACT

Substituted 1,3,4-thiadiazolinones of the formula (I),

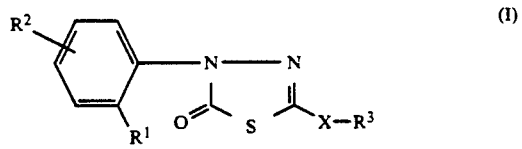

in which
X represents O or S,
$R^1$ represents hydrogen, alkyl, alkoxy, alkylthio, halogen, halogenoalkyl, halogenoalkoxy or halogenoalkylthio,
$R^2$ represents one or more identical or different radicals from the series comprising hydrogen, alkyl, alkoxy, alkylthio, halogenoalkyl, halogenoalkoxy, halogenoalkylthio, alkylenedioxy, halogenoalkylenedioxy, halogen, CN, $NO_2$, $NH_2$, alkylamino, dialkylamino, alkylcarbonyl, carbalkoxy, alkylsulphonyl, arylsulphonyl, sulphamoyl, alkylsulphamoyl, dialkylsulphamoyl, aryl, aryloxy and arylthio, each of which can, in turn, be substituted as well, and
$R^3$ represents alkyl, alkenyl or alkynyl, each of which can optionally be substituted, with the exception of the compound 5-methylmercapto-3-phenyl-1,3,4-thiadiazol-2-(3H)-one, are disclosed as being useful to combat endoparasites. Compositions containing these compounds, process for preparing them, and novel intermediates are also disclosed.

8 Claims, No Drawings

SUBSTITUTED 1,3,4-THIADIZAOLINONES, PROCESSES FOR THEIR PREPARATION, AND THEIR USE FOR COMBATING ENDOPARASITES

The present invention relates to new substituted 1,3,4-thiadiazolinones, to processes for their preparation, and to their use for combating endoparasites.

Substituted 2-alkoxy-1,3,4-oxathiazolinones and their use against endoparasites have already been disclosed, but their actions are not always satisfactory (DE-OS (German Published Specification) 2,604,110). 2-Aryloxy-1,3,4-oxadiazolinones have also previously been described (Pilgram, J. Heterocyclic Chem. 39, 823 (1982)); however, nothing is known about their use for combating endoparasites.

The present invention relates to substituted 1,3,4-thiadiazolinones of the formula (I),

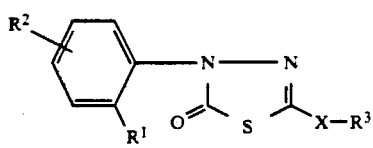

in which

X represents O or S, $R^1$ represents hydrogen, alkyl, alkoxy, alkylthio, halogen, halogenoalkyl, halogenoalkoxy or halogenoalkylthio, $R^2$ represents one or more identical or different radicals from the series comprising hydrogen, alkyl, alkoxy, alkylthio, halogenoalkyl, halogenoalkoxy, halogenoalkylthio, alkylenedioxy, halogenoalkylenedioxy, halogen, CN, $NO_2$, $NH_2$, alkylamino, dialkylamino, alkylcarbonyl, carbalkoxy, alkylsulphonyl, arylsulphonyl, sulphamoyl, alkylsulphamoyl, dialkylsulphamoyl, aryl, aryloxy and arylthio, each of which can, in turn, be substituted as well, and $R^3$ represents alkyl, alkenyl or alkynyl, each of which can optionally be substituted, with the exception of the compound 5-methylmercapto-3-phenyl-1,3,4-thiadiazol-2(3H)-one.

The present invention also relates to a process for the preparation of the new substituted 1,3,4-thiadiazolinones of the formula (I),

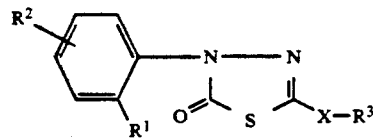

in which

X represents O or S, $R^1$ represents hydrogen, alkyl, alkoxy, alkylthio, halogen or halogenoalkyl, $R^2$ represents one or more identical or different radicals from the series comprising hydrogen, alkyl, alkoxy, alkylthio, halogenoalkyl, halogenoalkoxy, halogenoalkylthio, alkylenedioxy, halogenoalkylenedioxy, halogen, CN, $NO_2$, $NH_2$, alkylamino, dialkylamino, alkylcarbonyl, carbalkoxy, alkylsulphonyl, arylsulphonyl, sulphamoyl, alkylsulphamoyl, dialkylsulphamoyl, aryl, aryloxy and arylthio, each of which can, in turn, be substituted as well, and $R^3$ represents alkyl, alkenyl or alkynyl, each of which can optionally be substituted, with the exception of the compound 5-methylenemercapto-3-phenyl-1,3,4-thiadiazol-2(3H)-one, characterized in that compounds of the formula (II),

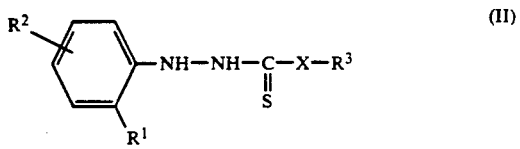

in which

X, $R^1$, $R^2$ and $R^3$ have the abovementioned meaning, are reacted with carbonylation reagents, such as phosgene, diphosgene or triphosgene, and the resulting compounds of the formula (III),

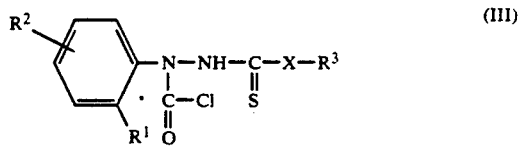

in which

X, $R^1$, $R^2$ and $R^3$ have the abovementioned meaning, are cyclized.

The present invention moreover relates to compounds of the formula (II),

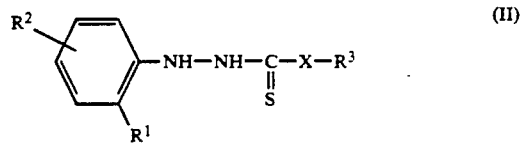

in which

X represents O or S, $R^1$ represents hydrogen, alkyl, alkoxy, alkylthio, halogen or halogenoalkyl, $R^2$ represents one or more identical or different radicals from the series comprising hydrogen, alkyl, alkoxy, alkylthio, halogenoalkyl, halogenoalkoxy, halogenoalkylthio, alkylenedioxy, halogenoalkylenedioxy, halogen, CN, $NO_2$, $NH_2$, alkylamino, dialkylamino, alkylcarbonyl, carbalkoxy, alkylsulphonyl, arylsulphonyl, sulphamoyl, alkylsulphamoyl, dialkylsulphamoyl, aryl, aryloxy and arylthio, each of which can, in turn, be substituted as well, and $R^3$ represents alkyl, alkenyl or alkynyl, each of which can optionally be substituted, which are new.

The present invention also relates to a process for the preparation of the compounds of the formula (II),

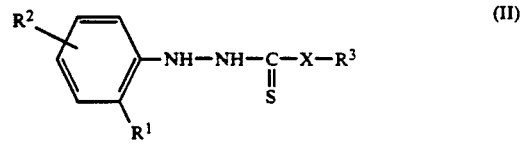

in which

X represents O or S, $R^1$ represents hydrogen, alkyl, alkoxy, alkylthio, halogen or halogenoalkyl, $R^2$ represents one or more identical or different radicals from the series comprising hydrogen, alkyl, alkoxy, alkylthio, halogenoalkyl, halogenoalkoxy, halogenoalkylthio, alkylenedioxy, halogenoalkylenedioxy, halogen, CN, $NO_2$, $NH_2$, alkylamino, dialkylamino, alkylcarbonyl, carbalkoxy, alkylsulphonyl, arylsulphonyl, sulphamoyl, alkylsulphamoyl, dialkylsulphamoyl, aryl, aryloxy and arylthio, each of which can, in turn, be substituted as well, and $R^3$ represents alkyl, alkenyl or alkynyl, each of which can optionally be substituted, characterized in that a) in the event that X represents S, phenylhydrazines of the formula (III),

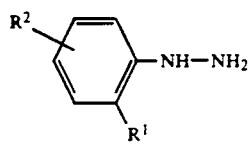
(III)

in which $R^1$ and $R^2$ have the abovementioned meaning, are reacted with carbon disulphide and compounds of the formula (IV)

$R^3$-Y  (IV)

in which

Y represents halogen or p-toluenesulphonyl and $R^3$ has the abovementioned meaning, or b) in the event that X represents O, compounds of the formula (V),

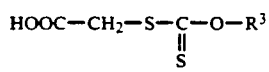
(V)

in which $R^3$ has the abovementioned meaning, are reacted with phenylhydrazines of the formula (VI),

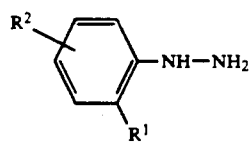
(VI)

in which $R^1$ and $R^2$ have the abovementioned meaning.

The compounds of the formula (I) are outstandingly suitable for combating endoparasites, in particular in the field of veterinary medicine.

Preferred compounds are those in which $R^1$ represents hydrogen, or halogen, preferably fluorine, chlorine, bromine or iodine; or represents alkyl having preferably 1 to 4, in particular 1 or 2, carbon atoms, such as methyl, ethyl, n.- and i.-propyl and n.-, i.-, s.- and t.-butyl; alkoxy having preferably 1 to 4, in particular 1 or 2 carbon atoms, such as methoxy, ethoxy, n.- and i.-propyloxy and n.-, i.-, s.- and t.-butyloxy; alkylthio having preferably 1 to 4, in particular 1 or 2, carbon atoms, such as methylthio, ethylthio, n.- and i.-propylthio and n.-, i.-, s.- and t.-butylthio; halogenoalkyl having preferably 1 to 4, in particular 1 or 2, carbon atoms and preferably 1 to 5, in particular 1 to 3, halogen atoms, the halogen atoms being identical or different and preferably representing fluorine, chlorine or bromine, in particular fluorine, such as trifluoromethyl, fluoroethyl or chloroethyl; halogenoalkoxy having preferably 1 to 4, in particular 1 or 2, carbon atoms and preferably 1 to 5, in particular 1 to 3, halogen atoms, the halogen atoms being identical or different and preferably representing fluorine, chlorine or bromine, in particular fluorine, such as trifluoromethoxy; halogenoalkylthio having preferably 1 to 4, in particular 1 or 2, carbon atoms and preferably 1 to 5, in particular 1 to 3, halogen atoms, the halogen atoms being identical or different and preferably representing fluorine, chlorine or bromine, in particular fluorine, such as trifluoromethylthio.

$R^2$ represents hydrogen, alkyl having preferably 1 to 4, in particular 1 or 2, carbon atoms, such as methyl, ethyl, n.- and i.-propyl and n.-, i.-, s.- and t.-butyl; alkoxy having preferably 1 to 4, in particular 1 or 2, carbon atoms, such as methoxy, ethoxy, n.- and i.-propyloxy and n.-, i.-, s.- and t.-butyloxy; alkylthio having preferably 1 to 4, in particular 1 or 2, carbon atoms, such as methylthio, ethylthio, n.- and i.-propylthio and n.-, i.-, s. -and t.-butylthio; halogenoalkyl having preferably 1 to 4, in particular 1 or 2, carbon atoms and preferably 1 to 5, in particular 1 to 3, halogen atoms, the halogen atoms being identical or different and preferably representing fluorine, chlorine or bromine, in particular fluorine, such as trifluoromethyl, fluoroethyl or chloroethyl; halogenoalkoxy having preferably 1 to 4, in particular 1 or 2, carbon atoms and preferably to 5, in particular 1 to 3, halogen atoms, the halogen atoms being identical or different and preferably representing fluorine, chlorine or bromine, in particular fluorine, such as trifluoromethoxy; halogenoalkylthio having preferably 1 to 4, in particular 1 or 2, carbon atoms and preferably 1 to 5, in particular 1 to 3, halogen atoms, the halogen atoms being identical or different and preferably representing fluorine, chlorine or bromine, in particular fluorine, such as trifluoromethylthio; in the case of phenyl, $R^2$ represents alkylenedioxy having preferably 1 or 2 carbon atoms, such as methylenedioxy or ethylenedioxy; in the case of phenyl, $R^2$ represents halogen-substituted alkylenedioxy having preferably 1 or 2 carbon atoms and preferably 1 to 4, in particular 2 to 3, halogen atoms, the halogen atoms being identical or different and preferably representing fluorine or chlorine, in particular fluorine, such as difluoromethylenedioxy, trifluoroethylenedioxy or tetrafluoroethylenedioxy. Other substituents are halogen, preferably fluorine, chlorine, bromine and iodine, in particular chlorine and bromine; cyano; nitro; dialkylamino having preferably 1 to 4, in particular 1 or 2, carbon atoms per alkyl group, such as dimethylamino, diethylamino or methyl-n.-butylamino; alkylcarbonyl having preferably 2 to 4 carbon atoms; carbalkoxy having preferably 2 to 4, in particular 2 or 3, carbon atoms, such as carbomethoxy and carboethoxy;

alkylsulphonyl having preferably 1 to 4, in particular 1 or 2, carbon atoms, such as methylsulphonyl and ethylsulphonyl; arylsulphonyl having preferably 6 or 10 aryl carbon atoms, such as phenylsulphonyl; and phenyl, naphthyl, phenoxy, naphthoxy, phenylthio and naphthylthio, each of which can, in turn, be substituted as well.

$R^3$ represents alkyl having preferably 1 to 4, in particular 1 or 2, carbon atoms, such as methyl, ethyl, n.- and i.-propyl and n.-, i.-, s.- and t.-butyl; alkenyl having 2 to 6, in particular 2 to 4, carbon atoms, such as vinyl and allyl, or alkynyl having 2 to 6, in particular 2 to 4, carbon atoms, it being possible for each of these substituents to be substituted, in turn, by one of the following radicals: alkoxy having preferably 1 to 4, in particular 1 or 2, carbon atoms, such as methoxy, ethoxy, n.- and i.-propyloxy and n.-, i.-, s.- and t.-butyloxy; alkylthio having preferably 1 to 4, in particular 1 or 2, carbon atoms, such as methylthio, ethylthio, n.- and i.-propylthio and n.-, i.-, s. -and t.-butylthio; halogenoalkyl having preferably 1 to 4, in particular 1 or 2, carbon atoms and preferably 1 to 5, in particular 1 to 3, halogen atoms, the halogen atoms being identical or different and preferably representing fluorine, chlorine or bromine, in particular fluorine, such as trifluoromethyl, fluoroethyl or chloroethyl; halogenoalkoxy having preferably 1 to 4, in particular 1 or 2, carbon atoms and preferably 1 to 5, in particular 1 to 3, halogen atoms, the halogen atoms being identical or different and preferably representing fluorine, chlorine or bromine, in particular fluorine, such as trifluoromethoxy; halogenoalkylthio having preferably 1 to 4, in particular 1 or 2, carbon atoms and preferably 1 to 5, in particular 1 to 3, halogen atoms, the halogen atoms being identical or different and preferably representing fluorine, chlorine or bromine, in particular fluorine, such as trifluoromethylthio; phenyl which is optionally substituted by alkylenedioxy having preferably 1 or 2 carbon atoms, such as methylenedioxy or ethylenedioxy; halogen-substituted alkylenedioxy having preferably 1 or 2 carbon atoms and preferably 1 to 4, in particular 2 to 3, halogen atoms, the halogen atoms being identical or different and preferably representing fluorine or chlorine, in particular fluorine, such as difluoromethylenedioxy, trifluoroethylenedioxy or tetrafluoroethylenedioxy. Other substituents are halogen, preferably fluorine, chlorine, bromine and iodine, in particular chlorine and bromine; cyano; nitro; alkylcarbonyl having preferably 2 to 4 carbon atoms; carbalkoxy having preferably 2 to 4, in particular 2 or 3, carbon atoms, such as carbomethoxy and carboethoxy; or alkylsulphonyl having preferably 1 to 4, in particular 1 or 2, carbon atoms, such as methylsulphonyl and ethylsulphonyl.

Particularly preferred compounds of the formula (I) are those in which

X represents O or S, $R^1$ represents hydrogen, or halogen, in particular chlorine or fluorine, $C_1$–$C_4$-alkyl, such as methyl or ethyl, $C_{1-4}$-alkoxy, such as methoxy or ethoxy, $C_{1-4}$-halogenoalkoxy, such as trifluoromethoxy, or $C_1$-halogenoalkylthio, such as trifluoromethylthio, $R^2$ represents hydrogen, or halogen, in particular chlorine, fluorine or bromine, $C_1$–$C_4$-alkyl, such as methyl or ethyl, $C_{1-4}$-alkoxy, such as methoxy or ethoxy, $C_{1-4}$-halogenoalkoxy, such as trifluoromethoxy, $C_{1-4}$-halogenoalkylthio, such as trifluoromethylthio, or nitro or cyano; carbalkoxy, such as carbomethoxy and carboethoxy; alkylsulphonyl, such as methylsulphonyl and ethylsulphonyl, and $R^3$ represents $C_1$-$C_4$-alkyl, such as methyl or ethyl, $C_{1-4}$-alkenyl, such as allyl, or $C_{1-4}$-alkynyl, such as propargyl, it being possible for this radical to be optionally substituted by halogen, such as chlorine, fluorine or bromine or phenyl.

Very particularly preferred compounds of the formula (I) are those in which

X represents O or S, $R^1$ represents hydrogen, halogen, in particular fluorine or chlorine, or $NO_2$, $CH_3$, $OCH_3$ or $CF_3$, $R^2$ represents hydrogen, halogen, in particular fluorine, chlorine or bromine, or $CH_3$, $OCH_3$, $NO_2$ or CN, and $R^3$ represents $C_{1-4}$-alkyl, in particular methyl or ethyl, or $C_{1-4}$-alkenyl, in particular allyl.

The following compounds of the formula (I) may be mentioned individually:

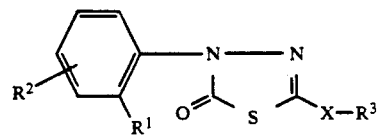

| $R^1$ | $R^2$ | $R^3$ | X |
|---|---|---|---|
| —Cl | —H | —$CH_3$ | S |
| —Cl | -6-Cl | —$CH_3$ | S |
| —Cl | -3-$CH_3$ | —$CH_3$ | S |
| —$CH_3$ | -3-$CH_3$ | —$C_2H_5$ | S |
| —F | —H | —$CH_3$ | S |
| —Cl | —H | —$C_2H_5$ | O |
| —$OCH_3$ | 4-Cl | —$CH_3$ | S |
| —Cl | -6-Cl | —$CH_3$ | O |
| —Cl | 4-Cl | —$C_2H_5$ | O |
| —F | —H | —$CH_2$—CH=$CH_2$ | S |
| —Cl | -3-Cl | —$CH_2$—CH=$CH_2$ | S |
| —$C_2H_5$ | —H | —$CH_2$—C≡CH | S |
| —$CH_3$ | 4-Cl | —$C_2H_5$ | O |
| —$CH_3$ | —H | —$CH_2$—$CH_2$—Cl | S |
| —$CH_3$ | 4,5 $Cl_2$ | —$C_2H_5$ | O |
| —$CF_3$ | —H | —$C_2H_5$ | S |
| —Cl | 4,5 $Cl_2$ | —$C_2H_5$ | O |
| —Cl | —H | —$CH_2$—C≡CH | S |
| —Cl | —H | -n$C_4H_9$ | S |
| —$CH_3$ | 3-$CH_3$ | -n$C_6H_{13}$ | S |
| —F | -6-F | -i$C_3H_7$ | O |

If in the preparation of the compounds of the formula (I) methyl 2-(2-chlorophenyl)-hyrazinethiocarboxylate is employed as the compound of the formula (II) and phosgene as the carbonylation reagent, the process may be represented by the following equation:

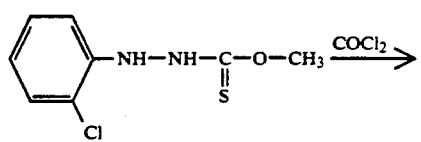

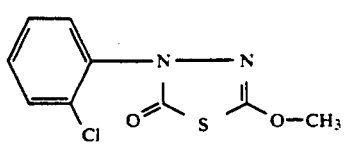

Compounds of the formula (II) which are preferably employed are those in which $R^1$, $R^2$, $R^3$ and X have the meanings indicated in the case of the compounds of the formula (I) as being preferred. The compounds of the formula (II) are new. Their preparation is described further below.

The following compounds of the formula (II) may be mentioned individually:

Methyl 2-(2-chlorophenyl)-dithiocarbazate, ethyl 2-(2,3-dimethylphenyl)-dithiocarbazate, methyl 2-(2-chlorophenyl)-hydrazinethionocarboxylate, ethyl 2-(2,5-difluorophenyl)-dithiocarbazate, allyl 2-(2,4-dichlorophenyl)-hydrazinethionocarboxylate, n-propyl 2-(2-methoxyphenyl)-dithiocarbazate, benzyl 2-(2-chloro-4-methylphenyl)-dithiocarbazate, n-hexyl 2-(2,3-dimethylphenyl)-hydrazinethionocarboxylate, ethyl 2-(2,4,6-trichlorophenyl)-hydrazinethionocarboxylate, propargyl 2-(2-bromophenyl)-dithiocarbazate, isopropyl 2-(2,3-dichloro-phenyl)-dithiocarbazate, ethyl 2-(2-ethyl-4-bromophenyl)-hydrazinethionocarboxylate, and n-propyl 2-(2,5-dichlorophenyl)-dithiocarbazate.

The reaction is carried out at temperatures from 20°-200° C. preferably at 50°-150° C., particularly preferably at the boiling point of the diluent.

Suitable diluents are all inert organic solvents. These include, in particular, aliphatic and aromatic, optionally halogenated hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, furthermore ethers, such as diethyl ether and dibutyl ether, glycol dimethyl ether and diglycol dimethyl ether, tetrahydrofuran and dioxane, moreover ketones, such as acetone, methyl ethyl ketone, methyl isopropyl ketone and methyl isobutyl ketone, in addition esters, such as methyl acetate and ethyl acetate, furthermore nitriles, such as, for example, acetonitrile and propionitrile, benzonitrile or gulatrodinitrile, moreover amides, such as, for example, dimethylformamide, dimethylacetamide and N-methylpyrrolidone, and also dimethyl sulphoxide, tetramethylene sulphone and hexamethylphosphoric triamide.

The cyclization can be carried out without a base or in the presence of a base.

Suitable bases are inorganic and organic bases. The following may be mentioned as bases: hydroxides, carbonates, hydrogen carbonates and alcoholates of alkali metals and alkaline earth metals, furthermore amines, such as, in particular, tertiary amines, for example trimethylamine, triethylamine, N-methylmorpholine, pyridine, picolines, N-ethylpyrrolidine, diazabicyclo(4,3,-0)undecene(DBU), 1,4-diazabicyclo(2,2,2)octane (DABCO), diazabicyclo(3,2,0)nonene (DBN) and ethyl-diisopropylamine.

The compounds of the formulae (II) and the bases are employed in a mutual ratio of 1:1 to 1:1.5. An approximately equimolar ratio is preferred.

After the reaction has been carried out, some of the diluent (approximately 50%) is distilled off, what remains is treated with aqueous acid, and the compounds of the formula (I) are isolated in a manner known per se by extracting them with a suitable solvent, for example ether or methylene chloride. The compounds of the formula I can subsequently be purified in a customary manner, for example by chromatography.

The compounds of the formula (II) are new. They are prepared by a process 4a) and 4b) analogously to the process described in Liebigs Ann. Chem. 735 (1970) p. 158 et seq. and U.S. Pat. No. 3,395,234.

The active compounds have a favorable toxicity to homothermals and are suitable for combating pathogenic endoparasites which are encountered in humans and in animal keeping and animal husbandry in livestock, breeding stock, zoo animals, laboratory animals, test animals and pets. They are active against all or individual development stages of the pests and against resistant and normally-sensitive species. By combating the pathogenic endoparasites, it is intended to reduce disease, deaths and reduced performance (for example the production of meat, milk, wool, hides, eggs, honey, etc), so that, by employing the active substances, more economical and simpler animal keeping is made possible. The pathogenic endoparasites include Cestodes, Trematodes, Nematodes and Acantocephala, in particular:

From the order of the Pseudophyllidea, for example Diphyllobothrium spp., Spirometra spp., Schistocephalus spp., Ligula spp., Bothridium spp., Diphlogonoporus spp..

From the order of the Cyclophyllidea, for example Mesocestoides spp., Anoplocephala spp., Paranoplocephala spp., Moniezia spp., Thysanosomsa spp., Thysaniezia spp., Avitellina spp., Stilesia spp., Cittotaenia spp., Andyra spp., Bertiella spp., Taenia spp., Echinococcus spp., Hydatigera spp., Davainea spp., Raillietina spp., Hymenolepis spp., Echinolepis spp., Echinocotyle spp., Diorchis spp., Dipylidium spp., Joyeuxiella spp., Diplopylidium spp..

From the subclass of the Monogenea, for example Gyrodactylus spp., Dactylogyrus spp., Polystoma spp..

From the subclass of the Digenea, for example Diplostomum spp., Posthodiplostomum spp., Schistosoma spp., Trichobilharzia spp., Ornithobilharzia spp., Austrobilharzia spp., Gigantobilharzia spp., Leucochloridium spp., Brachylaima spp., Echinostoma spp., Echinoparyphium spp., Echinochasmus spp., Hypoderaeum spp., Fasciola spp., Fasciolides spp., Fasciolopsis spp., Cyclocoelum spp., Typhlocoelum spp., Paramphistomum spp., Calicophoron spp·, Cotylophoron spp., Gigantocotyle spp., Fischoederius spp., Gastrothylacus spp., Notocotylus spp., Catatropis spp., Plagiorchis spp., Prosthogonimus spp., Dicrocoelium spp., Eurytrema spp., Troglotrema spp., Paragonimus spp., Collyriclum spp., Nanophyetus spp., Opisthorchis spp., Clonorchis spp., Metorchis spp., Heterophyes spp., Metagonimus spp..

From the order of the Enoplida, for example Trichuris spp., Capillaria spp., Trichomosoides spp., Trichinella spp..

From the order of the Rhabditia, for example Micronema spp., Strongyloides spp..

From the order of the Strongylida, for example Stronylus spp., Triodontophorus spp., Oesophagodontus spp., Trichonema spp., Gyalocephalus spp., Cylindropharynx spp., Poteriostomum spp., Cyclococercus spp., Cyclicostephanus spp., Oesophagostomum spp., Chabertia spp., Stephanurus spp., Ancylostoma spp., Uncinaria spp., Bunostomum spp., Globocephalus spp., Syngamus spp., Cyathostoma spp., Metastrongylus spp., Dictyocaulus spp., Muellerius spp., protostrongylus spp., Neostrongylus spp., Cystocaulus spp., Pneumostrongylus spp., Spicocaulus spp., Elaphostrongylus spp. Parelaphostrongylus spp., Crenosoma spp., Paracrenosoma spp., Angiostrongylus spp., Aelurostrongylus spp., Filaroides spp., Parafilaroides spp., Trichostrongylus spp., Haemonchus spp., Ostertagia spp., Marshallagia spp., Cooperia spp., Nematodirus spp., Hyostrongylus spp., Obeliscoides spp., Amidostomum spp., Ollulanus spp..

From the order of the Oxyurida, for example Oxyuris spp., Enterobius spp., Passalurus spp., Syphacia spp., Aspiculuris spp., Heterakis spp..

From the order of the Ascaridia, for example Ascaris spp., Toxascaris spp., Toxocara spp., Parascaris spp., Anisakis spp., Ascaridia spp..

From the order of the Spirurida, for example Gnathostoma spp., Physaloptera spp., Thelazia spp., Gongylonema spp., Habronema spp., Parabronema spp., Draschia spp., Dracunculus spp..

From the order of the Filariida, for example Stephanofilaria spp., Parafilaria spp., Setaria spp., Loa spp., Dirofilaria spp., Litomosoides spp., Brugia spp., Wuchereria spp., Onchocerca spp..

From the order of the Gigantorhynchida, for example Filicollis spp., Moniliformis spp., Macracanthorhynchus spp., Prosthenorchis spp..

The livestock and breeding stock include mammals, such as, for example, cattle, horses, sheep, pigs, goats, camels, water buffalos, donkeys, rabbits, fallow deer, reindeer, fur-bearing animals, such as, for example, minks, chinchilla or racoon, birds, such as, for example chickens, geese, turkeys or ducks, freshwater fish and sea fish, such as, for example, trout, carp and eels, reptiles and insects, such as, for example, honeybee and silk worm.

The laboratory and test animals include mice, rats, guinea pigs, golden hamsters, dogs and cats.

The pets include dogs and cats.

Administration can be effected prophylactically as well as therapeutically.

The active substances are administered, either directly or in the form of suitable preparations, enterally, parenterally, dermally, nasally, by treating the environment or with the aid of shaped articles containing the active compound, such as, for example, strips, plates, tapes, neck bands, ear tags, limb bands or marking devices.

Enteral administration of the active compound is effected for example orally in the form of powders, tablets, capsules, pastes, drinks, granules, solutions which can be applied orally, suspensions and emulsions, boli, medicated feed or drinking water. Dermal application is effected, for example, in the form of dipping, spraying, or pouring-on and spotting-on. Parenteral administration is effected, for example, in the form of injection (intramuscular, subcutaneous, intravenous or intraperitoneal) or by implants.

The following are suitable preparations:

Solutions, such as solutions for injection, oral solutions, concentrates for oral administration after dilution, solutions for use on the skin or in body cavities, pour-on formulations, gels;

Emulsions and suspension for oral or dermal administration and for injection; semi-solid preparations;

Formulations in which the active compound is incorporated in a cream base or in an oil-in-water or water-in-oil emulsion base;

Solid preparations, such as powders, premixes or concentrates, granules, pellets, tablets, boli, capsules; aerosols and inhalants, shaped articles containing the active compound.

Solutions for injection are administered intravenously, intramuscularly and subcutaneously.

Solutions for injection are prepared by dissolving the active compound in a suitable solvent and, if desired, adding additives, such as solubilizers, acids, bases, buffer salts, antioxidants, or preservatives. The solutions are sterile-filtered and decanted into containers.

The following may be mentioned as solvents: physiologically acceptable solvents, such as water, alcohols, such as ethanol, butanol, benzyl acohol, glycerol, propylene glycol, polyethylene glycols and N-methyl-pyrrolidone, and their mixtures.

If appropriate, the active compounds can also be dissolved in physiologically acceptable vegetable or synthetic oils which are suitable for injection.

The following may be mentioned as solubilizers: solvents which facilitate the dissolution of the active compound in the main solvent or which prevent precipitation of the active compound. Examples of solubilizers are polyvinylpyrrolidone, polyoxyethylated castor oil and polyoxyethylated sorbitan esters.

The following are preservatives: benzyl alcohol, trichlorobutanol, p-hydroxybenzoic esters or n-butanol.

Oral solutions are administered directly. Concentrates are first diluted to the administration concentration and then administered orally. Oral solutions and concentrates are prepared as described above in the case of the solutions for injection, sterile procedures not being necessary.

Solutions for use on the skin are applied drop by drop, smoothed on, rubbed in, splashed on or sprayed on. These solutions are prepared as described above in the case of the solutions for injection.

It may advantageous to add thickeners in the preparation process. The following are thickeners: inorganic thickeners, such as bentonites, colloidal silica, aluminium monostearate, or organic thickeners, such as cellulose derivatives, polyvinyl alcohols and their copolymers, acrylates and methacrylates.

Gels are applied to the skin or smoothed on or introduced into body cavities. Gels are prepared by adding such an amount of thickener to solutions which have been prepared as described in the solutions for injection that a clear composition is formed which has an ointment-like consistency. The thickeners used are the thickeners indicated further above.

Pour-on and spot-on formulations are poured or splashed onto limited areas of the skin, the active compound penetrating the skin and acting systemically.

Pour-on and spot-on formulations are prepared by dissolving, suspending or emulsifying the active compound in suitable solvents or solvent mixtures which are tolerated by the skin. If appropriate, other auxiliaries, such as colorants, resorption accelerators, antioxidants, light stabilizers or tackifiers.

The following may be mentioned as solvents: water, alkanols, glycols, polyethylene glycols, polypropylene glycols, glycerol, aromatic alcohols, such as benzyl alcohol, phenylethanol or phenoxyethanol, esters, such as ethyl acetate, butyl acetate or benzyl benzoate, ethers, such as alkylene glycol alkyl ethers, such as dipropylene glycol monomethyl ether or diethylene glycol mono-butyl ether, ketones, such as acetone or methyl ethyl ketone, aromatic and/or aliphatic hydrocarbons, vegetable or synthetic oils, DMF, dimethylacetamide, N-methyl-pyrrolidone, or 2,2-dimethyl-4-oxymethylene-1,3-dioxolane.

Colorants are all colorants which can be dissolved or suspended and which are released for use in animals.

Examples of resorption accelerators are DMSO, spreading oils, such as isopropyl myristate, dipropylene glycol pelargonate, silicone oils, fatty acid esters, triglycerides or fatty alcohols.

The following are antioxidants: sulphites or metabisulphites, such as potassium metabisulphite, ascorbic acid, butylhydroxytoluene, butylhydroxyanisole or tocopherol.

Examples of light stabilizers are novantisolic acid.

Tackifiers are, for example, cellulose derivatives, starch derivatives, polyacrylates or natural polymers such as alginates or gelatine.

Emulsions can be administered orally, dermally or as injections.

Emulsions are either the water-in-oil type or the oil-in-water type.

They are prepared by dissolving the active compound either in the hydrophobic or in the hydrophilic phase and by homogenizing this phase with the solvent of the other phase, with the aid of suitable emulsifiers and, if appropriate, other auxiliaries, such as colorants, resorption accelerators, preservatives, antioxidants, light stabilizers, and viscosity-increasing substances.

The following may be mentioned as the hydrophobic phase (oils): paraffin oils, silicone oils, natural vegetable oils such as sesame seed oil, almond oil or castor oil, synthetic triglycerides, such as caprylic/capric acid bigylceride, a triglyceride mixture with vegetable fatty acids of chain length $C_{8-12}$ or other specifically selected natural fatty acids, mixtures of partial glycerides of saturated or unsaturated fatty acids which may also contain hydroxyl groups, and mono- and diglycerides of the $C_8/C_{10}$-fatty acids.

Fatty acid esters, such as ethyl stearate, di-n-butyl-adipate, hexyl laurate, dipropylene glycol pelargonate, esters of a branched fatty acid having a medium chain length with saturated fatty alcohols of chain length $C_{16}-C_{18}$, isopropyl myristate, isopropyl palmitate, caprylic/capric esters of saturated fatty alcohols of chain length $C_{12}-C_{18}$, isopropyl stearate, oleyl oleate, decyl oleate, ethyl oleate, ethyl lactate, waxy fatty acid esters such as artificial duck uropygial fat, dibutyl phthalate, diisopropyl adipate, ester mixtures related to the latter, etc.

Fatty alcohols, such as isotridecyl alcohol, 2-octyldodecanol, cetylstearyl alcohol or oleyl alcohol.

Fatty acids, such as, for example, oleic acid and its mixtures.

The following may be mentioned as the hydrophilic phase: water, alcohols, such as, for example, propylene glycol, glycerol, sorbitol and their mixtures.

The following may be mentioned as emulsifiers: non-ionic surfactants, for example polyoxyethylated castor oil, polyoxyethylated sorbitan monooleate, sorbitan monostearate, glycerol monostearate, polyoxyethyl stearate or alkylphenol polyglycol ethers; Ampholytic surfactants, such as disodium N-lauryl-$\beta$-aminodipropionate or lecithin; Anionic surfactants, such as Na lauryl sulphate, fatty alcohol ether sulphates, and the monoethanolamine salt of mono/dialkylpolyglycol ether orthophosphoric ester; Cationic surfactants, such as cetyltrimethylammonium chloride.

The following may be mentioned as other auxiliaries: substances which increase the viscosity and stabilize the emulsion, such as carboxymethylcellulose, methylcellulose and other cellulose and starch derivatives, polyacrylates, alginates, gelatin, gum arabic, polyvinylpyrrolidone, polyvinylalcohol, methylvinyl ether/maleic anhydride copolymers, polyethylene glycols, waxes, colloidal silica, or mixtures of the listed substances.

Suspensions can be administered orally, dermally or as an injection. They are prepared by suspending the active compound in a liquid excipient, if appropriate with the addition of other auxiliaries, such as wetting agents, colorants, resorption accelerators, preservatives, antioxidants and agents which impart protection against light.

Liquid excipients which may be mentioned are all homogenous solvents and solvent mixtures.

Wetting agents (dispersants) which may be mentioned are the wetting agents indicated further above.

Other auxiliaries which may be mentioned are those indicated further above.

Semi-solid preparations can be administered orally or dermally. They are only distinguished from the above-described suspensions and emulsions by their higher viscosity.

To prepare solid preparations, the active compound is mixed with suitable excipients, if appropriate with the addition of auxiliaries, and the mixture is formulated as desired.

Excipients which may be mentioned are all physiologically acceptable solid inert substances. Suitable for this purpose are inorganic and organic substances. Inorganic substances are, for example, common salt, carbonates, such as calcium carbonate, hydrogen carbonates, aluminium oxides, silicas, clays, precipitated or colloidal silicon dioxide, and phosphates.

Organic substances are, for example, sugars, cellulose, foodstuffs and animal feeds, such as powdered milk, animal meals, cereal meals, coarse cereal meals and starches.

Auxiliaries are preservatives, antioxidants and colorants which have already been mentioned further above.

Other suitable auxiliaries are lubricants and gliding agents, such as, for example, magnesium stearate, stearic acid, talc, bentonites, disintegrants, such as starch or crosslinked polyvinylpyrrolidone, binders, such as, for example, starch, gelatin or linear polyvinylpyrrolidone, and dry binders, such as microcrystalline cellulose.

In the preparations, the active compounds can also be present in mixtures with synergists or other active compounds which are active against pathogenic endoparasites. Examples of such active compounds are L-2,3,5,6-tetrahydro-6-phenyl-imidazothiazole, benzimidazole carbamates, praziquantel, pyrantel or febantel.

Ready-to-use preparations contain the active compound in concentrations of 10 ppm to 20 per cent by weight, preferably from 0.1 to 10 per cent by weight.

Preparations which are diluted before use contain the active compound in concentrations of 0.5 to 90 per cent by weight, preferably from 5 to 50 per cent by weight.

In general, it has proved advantageous to administer amounts of about 1 to about 100 mg of active compound per kg of body weight per day, to achieve effective results.

Example A

In-vivo nematode test

Trichostrongylus colubriformis/sheep

Sheep which had been infected experimentally with Trichostrongylus colubriformis were treated after the prepatency time of the parasite had elapsed. The active compounds were administered orally as pure active compound in gelatin capsules.

The degree of effectiveness is determined by quantitatively counting the worm eggs excreted with the faeces before and after the treatment.

Complete disappearance of egg excretion after the treatment means that the worms were aborted or are damaged to such an extent that they no longer produce eggs (effective dose).

Active compounds which have been tested and effective administration rates (effective dose) can be seen from the table below.

| Active compound Example No. | Effective dose mg/kg |
|---|---|
| 2 | 25 |
| 3 | 25 |
| 1 | 25 |

Example B

In-vivo nematode test

Haemonchus contortus/sheep

Sheep which had been infected experimentally with Haemonchus contortus were treated after the prepatency time of the parasite had elapsed. The active compounds were administered orally as pure active compound in gelatin capsules.

The degree of effectiveness is determined by quantitatively counting the worm eggs excreted with the faeces before and after the treatment.

Complete disappearance of e99 excretion after the treatment means that the worms were aborted or are damaged to such an extent that they no longer produce eggs (effective dose).

Active compounds which have been tested and effective administration rates (effective dose) can be seen from the table below.

| Active compound Example No. | Effective dose mg/kg |
|---|---|
| 1 | 10 |
| 2 | 10 |
| 3 | 10 |

PREPARATION EXAMPLES

Example 1

Preparation of 3-(2,6-dichlorophenyl)-5-methylthio-1,3,4-thiadiazolin-2-one 10.9 g of a 20% solution of phosgene (0.022 mol) in toluene is added dropwise at room temperature to a solution of 5.35 g (0.02 mol) of methyl 2-(2,6-dichlorophenyl)-dithiocarbozate in 50 ml of toluene. Stirring is continued at room temperature for 2 hours, the solvent is distilled off in vacuo, and the residue is recrystallized from diisopropyl ether.

Yield: 4 g (68% of theory), m.p.: 139°–140° C.

Many of the products listed in the table below are obtained as oils after the solvent has been distilled off. They are purified by chromatography or by distillation.

The following compounds are prepared analogously to Example 1:

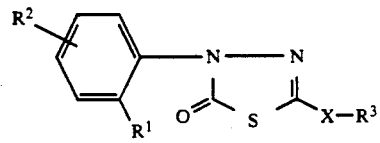

| Example | $R^1$ | $R^2$ | $R^3$ | X | Melting point | NMR data |
|---|---|---|---|---|---|---|
| 2 | —Cl | —H | —CH$_3$ | S | 49–50° | |
| 3 | —Cl | —H | —C$_2$H$_5$ | S | Öl | 1,4–1,5 ppm, t, 3H; 3,1 ppm, q, 2H |
| 4 | —Cl | —H | Allyl | S | Öl | 3,6 ppm, d, 2H; 5,4 ppm, m, 2H 5,9 ppm, m, 1H |
| 5 | —H | -3-Cl | —CH$_3$ | S | 67° | |
| 6 | —H | -3-Cl | —C$_2$H$_5$ | S | oil | 1,4–1,5 ppm, t, 3H; 3,2 ppm, q, 2H |
| 7 | —H | 4-Cl | —CH$_3$ | S | 67° | |
| 8 | —Cl | 4-Cl | —CH$_3$ | S | 71–72° | |
| 9 | —CH$_3$ | 4-Cl | —CH$_3$ | S | 89° | |
| 10 | —H | —H | —C$_2$H$_5$ | O | 38° | |
| 11 | —Cl | H | —C$_2$H$_9$ | O | 186° | |
| 12 | CH$_3$ | 3-CH$_3$ | CH$_3$ | S | 120° | |
| 13 | H | H | CH$_3$ | S | oil | |
| 14 | H | Br | CH$_3$ | S | 119° | |
| 15 | Cl | 3-Cl | CH$_3$ | S | 118° | |
| 16 | H | OCH$_3$ | CH$_3$ | | 81° | |
| 17 | H | 3-Br | CH$_3$ | S | 85° | |
| 18 | H | 4-Br | CH$_3$ | S | 90° | |
| 19 | H | 3-Cl, 4-CH$_3$ | CH$_3$ | S | 94° | |

What is claimed is:

1. A substituted 1,3,4-thiadiazolinone of the formula (I)

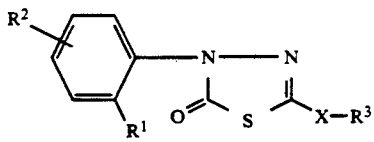

in which

X represents O or S;

$R^1$ represents hydrogen, halogen, C$_{1-4}$-alkyl, C$_{1-4}$-alkoxy, C$_{1-4}$-halogenoalkoxy, or C$_{1-4}$-halogenoalkylthio;

$R^2$ represents hydrogen, halogen, C$_{1-4}$-alkyl, C$_{1-4}$-alkoxy, C$_{1-4}$-halogenoalkoxy, C$_{1-4}$-halogenoalkylthio, nitro, cyano, carbalkoxy, or alkylsulphonyl; and $R^3$ represents C$_{1-4}$-alkyl, C$_{1-4}$-alkenyl, or C$_{1-4}$-alkynyl, each of which is unsubstituted or substituted by 1–5 halogen atoms, or phenyl.

2. The substituted 1,3,4-thiadiazolinone according to claim 1, in which

X represents O or S, $R^1$ represents hydrogen, halogen, or NO$_2$, CH$_3$, OCH$_3$ or CF$_3$, $R^2$ represents hydrogen, halogen, or $CH_3$, $OCH_3$, $NO_2$ or CN, and $R^3$ represents $C_{1-4}$-alkyl, or $C_{1-4}$-alkenyl.

3. The substituted 1,3,4-thiadiazolinone according to claim 1, in which

| $R^1$ is | $R^2$ is | $R^3$ is | X is |
|---|---|---|---|
| —Cl | —H | —$CH_3$ | S |
| —Cl | -6-Cl | —$CH_3$ | S |
| —Cl | -3-$CH_3$ | —$CH_3$ | S |
| —$CH_3$ | -3-$CH_3$ | —$C_2H_5$ | S |
| —F | —H | —$CH_3$ | S |
| —Cl | —H | —$C_2H_5$ | O |
| —$OCH_3$ | 4-Cl | —$CH_3$ | S |
| —Cl | -6-Cl | —$CH_3$ | O |
| —Cl | -4-Cl | —$C_2H_5$ | O |
| —F | —H | —$CH_2$—CH=$CH_2$ | S |
| —Cl | -3-Cl | —$CH_2$—CH=$CH_2$ | S |
| —$C_2H_5$ | —H | —$CH_2$—C≡CH | S |
| —$CH_3$ | 4-Cl | —$C_2H_5$ | O |
| —$CH_3$ | —H | —$CH_2$—$CH_2$—Cl | S |
| —$CH_3$ | 4,5 $Cl_2$ | —$C_2H_5$ | O |
| —$CF_3$ | —H | —$C_2H_5$ | S |
| —Cl | 4,5 $Cl_2$ | —$C_2H_5$ | O |
| —Cl | —H | —$CH_2$—C≡CH | S |
| —Cl | —H | —$nC_4H_9$ | S |
| —$CH_3$ | 3-$CH_3$ | —$nC_6H_{13}$ | S |
| —F | -6-F | —$iC_3H_7$ | O |

4. The substituted 1,3,4-thiadiazolinone according to claim 1, in which

| $R^1$ is | $R^2$ is | $R^3$ is | X is |
|---|---|---|---|
| Cl | Cl | —$CH_3$ | S |

-continued

| $R^1$ is | $R^2$ is | $R^3$ is | X is |
|---|---|---|---|
| —Cl | —H | —$CH_3$ | S |
| —Cl | —H | —$C_2H_5$ | S |
| —Cl | —H | Allyl | S |
| —H | -3-$CH_3$ | —$CH_3$ | S |
| —H | -3-Cl | —$C_2H_5$ | S |
| —H | -4-Cl | —$CH_3$ | S |
| —Cl | 4-Cl | —$CH_3$ | S |
| —$CH_3$ | 4-Cl | —$CH_3$ | S |
| —H | —H | —$C_2H_5$ | O |
| —Cl | H | —$C_2H_9$ | O |
| $CH_3$ | 3-$CH_3$ | $CH_3$ | S |
| H | H | $CH_3$ | S |
| H | Br | $CH_3$ | S |
| Cl | 3-Cl | $CH_3$ | S |
| H | $OCH_3$ | $CH_3$ | |
| H | 3-Br | $CH_3$ | S |
| H | 4-Br | $CH_3$ | S |
| H | 3-Cl,4-$CH_3$ | $CH_3$ | S |

5. A composition useful to combat endoparasites, which comprises a carrier and a substituted 1,3,4-thiadiazolinone according to claim 1 in an amount effective to combat endoparasites.

6. A method of combating endoparasites, which comprises administering to a patient a substituted 1,3,4-thiadiazolinone according to claim 1 in an amount effective to combat endoparasites.

7. A method of combating endoparasites, which comprises administering to a patient a substituted 1,3,4-thiadiazolinone according to claim 3 in an amount effective to combat endoparasites.

8. A method of combating endoparasites, which comprises administering to a patient a substituted 1,3,4-thiadiazolinone according to claim 4 in an amount effective to combat endoparasites.

* * * * *